United States Patent [19]

Modrovich

[11] 4,277,562
[45] Jul. 7, 1981

[54] STABILIZED LIQUID ENZYME AND COENZYME COMPOSITIONS

[76] Inventor: Ivan E. Modrovich, 1043 Mesa Dr., Camarillo, Calif. 93010

[21] Appl. No.: 862,678

[22] Filed: Dec. 20, 1977

Related U.S. Application Data

[63] Continuation-in-part of Ser. No. 722,565, Sep. 13, 1976, abandoned.

[51] Int. Cl.³ .......................... C12Q 1/50; C12N 9/96
[52] U.S. Cl. ........................................ 435/17; 435/15; 435/26; 435/188; 435/190; 435/194
[58] Field of Search .............. 195/63, 68, 99, 103.5 R; 435/4, 17, 188, 15, 26, 190, 194

[56] References Cited

U.S. PATENT DOCUMENTS

| | | | |
|---|---|---|---|
| 3,540,984 | 11/1970 | Deutsch | 195/63 X |
| 3,557,002 | 1/1971 | McCarty | 195/63 X |
| 3,627,688 | 12/1971 | McCarty et al. | 195/63 X |
| 3,764,478 | 10/1973 | Bergmeyer et al. | 195/99 |
| 3,776,900 | 12/1973 | Hammer | 195/63 X |
| 3,778,350 | 12/1973 | Bergmeyer et al. | 195/99 X |

OTHER PUBLICATIONS

George et al., Stabilization of Lactate and Malate Dehydrogenase by Organic Solvents, Biochim. Biophys. Acta., vol. 191, 1969, (pp. 466-468).

*Primary Examiner*—David M. Naff
*Attorney, Agent, or Firm*—Romney, Schaap, Golant, Disner & Ashen

[57] ABSTRACT

A multi-reagent for use in stabilized liquid form is prepared containing three separate reagent solutions which can be combined in proper amounts to form a working composition for a biological diagnostic determination. The first reagent solution contains an aqueous vehicle, organic solvent and coenzyme; the second reagent solution contains an aqueous vehicle, organic solvent, enzyme and substrate; and the third reagent solution contains an aqueous vehicle, buffering agent and an additional component such as a sulphydryl compound.

56 Claims, No Drawings

STABILIZED LIQUID ENZYME AND COENZYME COMPOSITIONS

RELATED APPLICATION

This application is a continuation-in-part application of Application Ser. No. 722,565, filed Sept. 13, 1976, now abandoned in favor of copending continuation Patent Application Ser. No. 940,941, filed Sept. 11, 1978.

BACKGROUND OF THE INVENTION

1. Field of the Invention

This invention relates in general to certain new and useful improvements in biological determination reagent composition which permits the stabilization of enzymes and coenzymes in an aqueous media therein, and the method of stabilizing, and, more particularly, to such reagent composition and methods useful in determination of creatine phosphokinase.

2. Description of the Prior Art

It has recently been estimated that 25% of all in vitro diagnostic tests conducted annually in this country are not reliable. Unreliable tests can result in unnecessary medical treatment, the withholding of necessary treatment and lost income. Because of their high specificity, the use of enzyme determinations has significantly increased during the last few years, and indications are that this trend will continue. However, rigorous quality control measures are required to assure the accuracy and consistency of results. This requirement stems from the fact that the exact nature of enzymes, as well as the mechanisms of their action, remains unknown for the most part.

At present, the greatest limitation on the enzyme reagent manufacturer, by far, lies in the unstable characteristics of his products. Current methodologies require the use of numerous labile ingredients, and these ingredients are more likely to increase, rather than decrease, in number. Due to these severe restraints, rigorous quality control is required, and this quality control is, of course, costly. Moreover, if control in any step in the process is not maintained within high degree of control standards, the quality of the final product can be reduced materially.

The present commercial state of the art used for stabilizing the reactive ability of enzymes or coenzymes is by locking them into a solid matrix, either by freeze drying, dry blending such as used for tableting dried powders, primarily in the pharmaceutical diagnostic and related industries and immobilization by locking the chemical structure of the enzyme into a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending, and usefulness of the product is further limited by packaging modes and sizes.

Furthermore, good product uniformity is difficult to achieve. This condition is exemplified by the fact that most commercial freeze dried control sera (reference serum) lists the acceptable bottle-to-bottle variation of enzyme constituents at ±10% of the mean.

The present invention is uniquely designed so that the labile ingredients in a diagnostic reagent composition are effectively stabilized. The composition comprises three separate solutions and the first of which is a substrate solution which contains a labile substrate and at least one labile enzyme. The second solution is a coenzyme solution which contains at least one labile coenzyme and may contain a labile enzyme. The third solution is a buffer solution which includes a buffer agent to maintin the desired pH when the three solutions are mixed at time of use. The labile components are effectively stabilized in aqueous solutions against reactivity, and the means of stabilization ensures long-term stability in a liquid media. Moreover, close tolerance control can be achieved in the manufacturing of a high quality product which eliminates the inconvenience of the rigid package size and the high cost of packaging and freeze drying and reagent waste.

OBJECTS OF THE INVENTION

It is, therefore, the primary object of the present invention to provide a liquid composition comprised of a first substrate-enzyme solution, a second coenzyme solution and a third buffer solution and where the labile components therein are stabilized and mixed prior to use.

It is an additional object of the present invention to provide a stabilized composition of the type stated where the substrate-enzyme solution and the coenzyme solution can be stabilized in the presence of an organic solvent.

It is another object of the present invention to provide a composition of the type stated which has excellent shelf life and in which the containers of each of the solutions may be repeatedly opened without substantial degradation of the labile components therein.

It is yet another object of the present invention to provide a stabilized liquid composition which may be stored in an aqueous media, and which includes enzyme inhibitors to compensate for undesired reactivity of certain contaminant enzymes in the composition and all of which are stabilized against degradation.

It is a further object of the present invention to provide a labile enzyme and coenzyme composition of the type stated in an aqueous organic solvent media and where the stabilization of the enzyme and coenzyme does not affect the enzymatic reactivity after a substantial period of time.

It is also an object of the present invention to provide a method of stabilizing labile enzymes and/or coenzymes in a liquid media with relatively low-cost, commercially available stabilizing ingredients.

It is yet a further object of the present invention to provide a method of stabilizing enzymes and/or coenzymes in the presence of a liquid media for a substantial period of time with a high degree of composition purity.

With the above and other objects in view, my invention resides in the novel compositions and the methods of making the same as hereinafter described in more detail.

SUMMARY OF THE INVENTION

The present invention provides a biological determination reagent composition for determining biological constituents in a biological fluid. The composition is comprised of three aqueous solutions referred to as a "coenzyme solution", a "substrate solution", and a "buffer solution".

The labile enzymes, coenzymes and substrates and other labile components are treated according to the invention, resulting in long-term stability without affecting enzymatic or coenzymatic reactivity or photometric absorptivity. The invention provides reagents where quality control is assured throughout manufacturing, packaging, storage and use. The inconvenience of rigid package size is eliminated as is the high cost of packaging, freeze drying and reagent waste. The liquid enzyme, coenzyme and substrate systems provide application flexibility and separation of the ingredients is easily accomplished with neglgible manufacturing cost providing the flexibility of triggering the desired reaction after all side reactions have been dissipated.

The stabilized labile components of the invention have been assessed in studies which compared respectivve liquid enzyme and liquid coenzyme reagents with fresh reagents. The studies show a 1:1 correlation between aged liquid and fresh reagents with comparable sensitivity and precision. Providing enzyme and coenzyme reagents in a stable liquid form enhances the colorimetric applicability of present day NAD/NADH coupled methodologies, as well as other methodologies, primarily because the separation of ingredients is easily accomplished. Stable liquid reagents are especially advantageous where NADH and other coenzyme consumption is the basis of measurement in the determination of creatine phosphokinase (CPK), and the color reagent must be separated from the NADH and the reaction main. In the ultraviolet mode, the liquid system offers better reagent homogeneity and packaging, as well as flexibility in usage, in contrast to the freeze-dried or dry media preparation.

In diagnostic enzymology, the stabilization of enzyme and coenzyme reagents in a ready-to-use liquid media is a new and exciting approach to satisfy the needs of the clinical laboratory and the reliability demands of the regulatory authorities. The flexibility of liquid enzyme and coenzyme systems ensures their applicability to automated instrumentation, as well as their convenience in manual testings.

The liquid media which is designed to provide for stabilization of enzymes and coenzymes as hereinafter described is uniquely formulated so that one or more coenzymes may be stabilized in the media. Otherwise, one or more enzymes may be stabilized in the liquid media. Moreover, both coenzymes and enzymes may be stabilized in the same liquid media in a single container.

In Applicant's copending Application Ser. No. 722,565, filed Sept. 13, 1976, certain specified liquid stabilized enzyme and coenzyme reagent compositions and the methods for producing the same were described. Certain of these compositions are effective in the biological determination of CPK. However, it has now been found that a highly effective three reagent solution forming the composition can be used in the determination of CPK and like constituents. In this way, it is possible to effectively make a determination after the CPK is added without inhibition of the determination, even in the presence of the stabilizing agents.

The prior art has known of compositions in which labile coenzymes, such as NADH for example, were stabilized in the presence of a polyol in a high concentration. In like manner, the prior art has known of compositions in which labile enzymes, such as MDR or LDR, were stabilized in the presence of a relatively small concentration of a polyol. A polymer was also used in the stabilization process. Moreover, these compositions could also be used in the determination of CPK and biological constituents and other enzymes.

However, these prior art compositions are not as effective as the compositions described herein. In the case of the present invention, a gelatin polymer or other form of polymer is not necessarily required with certain of the enzymes and coenzymes due to the fact that the organic solvent may be used in a much greater quantity.

The solution which is termed the substrate solution or substrate reagent will generally contain the substrate ADP along with creatine phosphate, the cofactor AMP and the enzyme glucose-6-PDH, and these components are stabilized in the presence of an organic solvent such as glycerol with an alkaline pH of about 7 to 10. The solution which is termed the buffer solution or buffer reagent will contain the sugar, glucose, and a buffering agent, such as imidazole, and is stabilized in an acid pH in the range of about 5 to 7.0. The buffer solution will also normally include a magnesium activator such as magnesium acetate, an R-SH compound, namely compounds having sulfohydryl groups, namely mercaptans as for example dithiothreitol, and a polymer, such as dextran. The solution which is termed the coenzyme solution or coenzyme reagent will normally contain NAD, or otherwise an NADP coenzyme along with the enzyme hexokinase and a coenzyme or cofactor AMP which are stabilized in the presence of an organic solvent, such as glycerol, and at an acid pH. The coenzyme solution may also contain a sulfohydryl compound such as N-acetyl cysteine.

It should be understood that while the three solutions are referred to as "buffer", "substrate" and "coenzyme" solutions, they may not only respectively contain a buffer, a substrate and a coenzyme, exclusively. Thus, the coenzyme solution may contain one or more substrate and the enzyme solution may contain one or more coenzymes and the buffer solution may contain either or both enzymes or coenzymes. The three solutions or reagents are so named due to the fact that the coenzyme solution is primarily designed to stabilize at least a certain coenzyme and the substrate solution is primarily designed to stabilize at least a certain substrate. The buffer solution, as indicated above, is designed primarily to maintain a proper pH in the final composition, and to stabilize the sulfohydryl compound.

After the liquid stabilized solutions are prepared, they are then dispensed into individual amber-glass bottles and which are sealed in an air-tight condition. Moreover, these bottles are typically stored under refrigeration. The projected shelf life of the stabilized enzymes and coenzymes is up to two years under these conditions without significant degradation.

It has been found in accordance with the present invention that the enzymes, coenzymes, substrates and other labile components exhibit good solubility and stability in the aqueous miscible organic solvent. The envisioned chemical or physical reaction which provides for the stabilization is more fully described hereinafter.

These and other features and attendant advantages of the invention will become apparent as the invention becomes better understood by reference to the following general description and the following detailed description.

DETAILED DESCRIPTION

In the clinical diagnostic field, the commercial application of the present invention is represented by, but not limited to, the diagnostic reagents used to determine enzymatic activity in biological constituents, as for example, creatine phosphokinase. The diagnostic reagents of the invention can also be used for determining substrate concentration, as for example, glucose concentrations in biological fluids, and the like. Nevertheless, compositions prepared in accordance with the present invention can be used to determine and quantitate other biological constituents, as for example, the following constituents in biological fluids:

1. Glutamic-oxalacetic transaminase (SGOT)
2. Glutamic-pyruvic transaminase (SGPT)
3. Lactic dehydrogenase (LDH-P)
4. Lactic dehydrogenase (LDH-L)
5. Creatine Phosphokinase (CPK)
6. a-Hydroxybuteric dehydrogenase (a-HBD)
7. Glucose (via Hexokinase-G-6-PDH)

These above identified reagents often react similarly, contain some common labile ingredients, and some of the chemical reactions involved are common. The following chemical reaction scheme is presented as a model to illustrate the general nature of the reactions involved:

REACTION SCHEME 1—GENERAL MODEL $$\text{SUBSTRATE(S)} \underset{}{\overset{\text{ENZYME}_1}{\rightleftharpoons}} \text{PRODUCT(S)} \quad (1)$$

$$\text{PRODUCT/SUBSTRATE} + \text{NAD} - \quad (2)$$
$$\text{NADH}_2 \underset{}{\overset{\text{ENZYME}_2}{\rightleftharpoons}} \text{NADH}_2 - \text{NAD} + \text{PRODUCT}$$

$$\text{NADH} + \text{CHROMOGEN} \underset{(\text{oxidized})}{\overset{\text{CATALYST}}{\rightleftharpoons}} \text{CHROMOGEN} + \text{NAD}$$
$$(\text{reduced})$$

All enzymatic reactions listed above, in accordance with this invention, will follow this general scheme, where reaction (2) is usually referred to as the coupling reaction, reactions (2) and (3) are the measuring reactions, and reaction (1) may be characterized as the primary reaction. It is understood, however, that not all three reactions are required for measurement; in fact, they may be limited to two, or one. In the case of the ultraviolet measurement of lactic dehydrogenase (LD) activity, for example, only reaction (2) is involved, as follows:

REACTION SCHEME 2—LDH $$\text{LACTATE} + \text{NAD} \underset{}{\overset{\text{LDH}}{\rightleftharpoons}} \text{NADH}_2 + \text{PYRUVATE}$$

REACTION SCHEME 3—GLUCOSE

The following reactions illustrate the determination of glucose by utilization of the coenzymes ATP and NAD.

$$\text{GLUCOSE} + \text{ATP} \underset{\text{Mg}^{++}}{\overset{\text{HK}}{\rightleftharpoons}} \text{G-6-P} + \text{ADP}$$

$$\text{G-6-P} + \text{NAD} \underset{}{\overset{\text{G-6-PDH}}{\rightleftharpoons}} \text{NADH} + \text{6-PHOSPHOGLUCONOLACTONE}$$

$$\text{NADH} + \text{INT} \underset{(\text{OX})}{\overset{\text{PMS}}{\rightleftharpoons}} \text{NAD} + \text{INT}$$
$$(\text{RED.})$$

More than the three reactions listed are involved, as in the case of creatine phosphokinase (CPK):

REACTION SCHEME 4—CPK $$\text{CP} + \text{ADP} \underset{}{\overset{\text{CPK}}{\rightleftharpoons}} \text{ATP} + \text{CREATINE} \quad (1)$$

$$\text{ATP} + \text{GLUCOSE} \underset{\text{Mg}^{++}}{\overset{\text{HK}}{\rightleftharpoons}} \text{GLUCOSE-6-PHOS.} + \text{ADP} \quad (2)$$

$$\text{GLUCOSE-6-PHOS.} + \text{NAD} \underset{}{\overset{\text{G-6-PDH}}{\rightleftharpoons}} \text{NADH} + \text{6-PHOSPHOGLUCONOLACTONE} \quad (3)$$

$$\text{NADH}_2 + \text{INT} \underset{(\text{OX})}{\overset{\text{PMS}}{\rightleftharpoons}} \text{INT} + \text{NAD} \quad (4)$$
$$(\text{RED.})$$

Referring to REACTION SCHEME 1—GENERAL MODEL, it becomes obvious and is general knowledge that the use of the reaction sequence permits the analytical quantitation of either the reaction substrates/procducts or the catalyzing enzymes. In this case, reactions (2) and/or (3) may be considered the coupling reactions, reactions (3) and/or (4) the measuring reactions, and reaction (1) the primary reaction.

In the above REACTION SCHEME 3, the enzyme which causes the primary reaction is hexokinase, and the enzyme which causes the coupling and measuring reaction is G-6-PDH. In the above REACTION SCHEME 3, the glucose is determined by measuring the NADH which is formed in the measuring reaction. In essence, the reaction is permitted to go to completion, and the amount of the coenzyme NADH formed is essentially measured. In the determination of CPK, considering REACTION SCHEME 4, the rate at which ATP is produced may be measured, as hereinafter described.

The symbols which have been used above and which are used hereinafter represent the following constituents:

CP = creatine phosphate
CPK = creatine phosphokinase
ADP = adenosin-5′-diphosphate
AMP = adenosine monophosphate
ATP = adenosine triphosphate
HK = hexokinase
NAD = nicotinamide-adenine dinucleotide
NADP = nicotinamide-adenine dinucleotide phosphate
NADH$_2$ = nicotinamide-adenine dinucleotide, reduced
G-6-PDH = glucose-6-phosphate dehydrogenase
G-6-P = glucose-6-phosphate
INT = tetrazolium salt
PMS = phenazine methosulfate In the determination of many enzymes and other biological constituents, as in the determination of CPK, enzymes, coenzymes and substrates are all involved in the reaction media, as indicated above.

Enzymes are large molecular weight, complex protein molecules, usually of unknown chemical structure. They are presently classified by their catalytic activity and extreme substrate specificity. Enzymes may be redefined as biological catalysts, capable of catalyzing a reaction of a single substrate, or a reaction of a similar group of substrates.

Coenzymes are lower molecular weight organic chemicals of well-defined structure, whose reactions or interactions are necessary for specific enzyme assay or reaction. They are catalyzed resulting in an irreversible change in the coenzyme's structure and/or atomic composition. Coenzymes are very useful in clinical assay procedure. Some have strong absorbance, their reactions are stoichiometric with the substrate and, therefore, the creation or disappearance of the absorbing form can be followed photometrically. Nicotinamide-adenine dinuceotide (NAD) and its reduced form (NADH$_2$) are used in many important clinical assays such as the S.G.O.T., S.G.P.T. and LDH assays previously described. NAD and NADH$_2$ have a molecular weight of about 700 and are complex organic molecules. NADH$_2$ absorbs strongly at 340 nm, whereas NAD does not absorb at this wavelength.

Substrates are organic chemicals of known structure, whose reactions or interactions are catalyzed by enzymes resulting in a change in the compound's structure, atomic composition, or stereochemical rotation. In general, substrates will chemically degrade or hydrolyze in an aqueous medium and are prone to microbiological degradation as they serve as food for bacteria, fungi and other microorganisms. Typical substrates are glucose, lactate or lactic acid, gluconate and the like.

SUBSTRATE REAGENT

The substrate solution or substrate reagent is comprised of the substrate creatine phosphate, neucleotides, such as ADP and AMP, often referred to as coenzymes or cofactors, and the enzyme G-6-PDH. In many cases, it is desirable to employ a bacteriostatic or fungicidal agent, as for example, an azide compound. Stabilization is achieved by addition of a suitable organic solvent, such as glycerol.

In order to form the substrate composition, the glycerol, or other organic solvent, is usually added to water so that the organic solvent is present in an amount of about 30% v/v in the aqueous solution, although the organic solvent can range from about 10% to about 50% v/v, and preferably from about 20% to about 40% v/v. The aqueous medium is maintained at a temperature within the range of about 15°–30° C., and preferably 20° C.–25° C., during the addition of the various components.

After the addition of the glycerol or other organic solvent, the pH is adjusted to the range of about 7 to 10, although the preferred range is about 8 to 9. At present, the most desirable pH is about 8.2. The pH may be adjusted by the addition of a suitable alkaline material, such as sodium hydroxide or the like. In addition, if desired, a suitable buffering agent, such as a tris buffer, may be used to adjust the pH and is typically added in about 0.05 molar to about 0.5 molar.

The creatine phosphate is generally added in the range of about 100 millimolar to about 300 millimolar, and preferably about 200 to about 300 millimolar. One of the most preferred amounts is about 260 millimolar for the creatine phosphate. The ADP is thereafter added in a range of 5 millimolar to about 50 millimolar, and preferably about 10 millimolar to about 25 millimolar, although the most preferred amount is about 18 millimolar. In like manner, the AMP is added in a range of 5 millimolar to about 50 millimolar, and preferably about 10 millimolar to about 25 millimolar, although the most preferred amount is about 20 millimolar. The neucleotides generally serve as inhibitors of an undesired side reaction involving the enzyme myokinase, as hereinafter described. Prior to the addition of the enzyme G-6-PDH, the pH should again be adjusted to the desired range of about 8 to 9, and preferably 8.2.

After the addition of the substrates and the cofactor, and readjustment of the pH, the enzyme G-6-PDH may be added and is usually present in an amount of about 5000 I.U. (International Units) per liter to about 100,000 I.U. per liter. Generally, the limitation on the upper amount of the enzyme is the amount of contaminants present in the commercial preparation of the enzyme, as for example, the contaminant enzyme, myokinase, as well as the cost factor. It is preferred to add the G-6-PDH in an amount of about 10,000 to about 50,000 I.U., although the preferred amount is about 20,000 to about 30,000 I.U. per liter. The most preferred amount is about 25,000 I.U. per liter. The G-6-PDH should, preferably, be formed by the L-mesenteroides bacteria if NAD coenzyme is used, or G-6-PDH by yeast if NADP is used, and should be concentrated in the range specified above.

Optionally, a bactericidal or fungicidal agent, preferably, an azide compound, such as sodium azide, may be added to the substrate solutions, typically in an amount of about 0.1% w/w. However, the amount of azide or other bactericidal or fungicidal compound which is added can range from 0.01% to about 0.5%. Thus, in certain cases, the organic solvent in the aqueous media in this solution may be generally insufficient to provide the required stabilization of the labile components against microbial action. In other cases, where the organic solvent concentration is sufficiently high, e.g. 40% v/v or greater, to prevent microbial growth, the azide salt or other bacteriostatic or fungicidal agent is not necessary and can be eliminated.

In addition to the foregoing, other bactericidal or other fungicidal agents which do not chemically react with a substrate or inhibit the enzymatic reaction may be employed. For example, some of these agents which may be used in addition to sodium azide are benzoic acid, phenol, thymol or pentachlorophenol.

In many cases, the suitable organic solvent, as for example, glycerol, may be added after or before adjustment of the pH. The organic solvent should have the following characteristics:

1. pH range of 4 to 10;
2. liquid at room and/or refrigerator temperatures;
3. does not react with NAD or ATP and the like other than forming electrostatic (i.e., hydrogen) bonds;
4. miscible with water;
5. standard free energy of solvolysis is low (normal resonance is established).

The solvent must be miscible with water and nondegradatively reactive with reactive sites of the enzymes and coenzymes other than formation of electrostatic bonds. Useful solvents are generally stable organic solvents such as ethers, ketones, sulfones, sulfoxides and alcohols such as methanol, ethanol, propanol, butanol, acetone, dioxane, DMSO, dimethylsulfone and THF. However, higher activity at lower solvent concentration for the treatment step is found for liquid polyol solvents. Liquid polyols containing from 2–4 hydroxyl groups and 2–10 carbon atoms are preferred, such as glycerol, ethylene glycol, propylene glycol or butane diol. Glycerol, propylene glycol, 1,2-propanediol, were found to possess all these qualities and are the solvents of choice.

COENZYME REAGENT

The coenzyme solution or coenzyme reagent generally includes the coenzyme NAD or otherwise the coenzyme NADP along with the coenzyme AMP in an aqueous medium. The coenzyme solution will also include the enzyme hexokinase, and will similarly be stabilized in an organic solvent, such as glycerol, and at an acid pH.

In order to form the coenzyme solution, the suitable organic solvent is added to water such that the organic solvent, such as glycerol is present in a range of about 15% v/v to about 65% v/v, although preferably the organic solvent is added in a range of about 35% v/v to about 55% v/v. In the most preferred aspect, the organic solvent is glycerol and is present in an amount of 50% v/v. However, any of the other organic solvents mentioned above may be used. Thereafter, the coenzyme NAD, or otherwise the coenzyme NADP may be added in a range of about 20 millimolar to about 500 millimolar, and preferably from about 50 millimolar to about 150 millimolar. In the preferred aspect, the coenzyme NAD or NADP should be present in an amount of about 100 millimolar.

The NAD coenzyme is actually more stable in the acid environment and it has also been found that the NAD does not even materially degrade in a slightly basic environment at a pH of about 7.5. The NAD may be added in considerable excess so that there is always sufficient undegraded NAD present, even after several years of storage in this liquid environment.

After the addition of the NAD, or otherwise the NADP, the inhibiting coenzyme AMP is also added. In this case, the coenzyme AMP should be added in an amount sufficient to constitute a concentration at least two to two and a half times greater than the ADP which will be present in the final composition when initially mixed. Thus, the AMP is preferably added in a range of about 20 millimolar to about 200 millimolar and preferably at about 35 millimolar to about 100 millimolar. In the most preferred aspect, the AMP is added in an amount of about 86 millimolar.

As indicated previously, AMP was added to the substrate reagent along with the ADP. Generally, it is desirable to have both ADP and AMP in the reaction media during an assay in order to avoid the effects of the myokinase enzyme as hereinafter described. Thus, ADP could be incorporated in the substrate reagent and AMP in the coenzyme reagent or in reverse. In like manner, the AMP and ADP could be incorporated in only one of the reagents. However, it is highly desirable to have the AMP and ADP present in each solution where the undesirable myokinase enzyme may be present.

Thus, in this embodiment of the present invention, after the addition of the NAD, or otherwise the NADP, the inhibiting coenzyme ADP is also added. Here, again, the coenzyme ADP should be added in an amount so that the AMP is present in a concentration at least two to two and a half times greater than the ADP in the final composition when initially mixed.

As indicated previously, the neucleotides AMP and ADP, and for that matter the neucleotide ATP, are often referred to herein as coenzymes or cofactors even though they are classicially neucleotides. Thus, the ADP, ATP and AMP will be referred to as coenzymes or cofactors herein to conform to nomenclature often used for those compounds and since they do in fact constitute an integral and important part of a coenzyme structure.

As also indicated previously, the sulfohydryl compound could be added to the coenzyme solution as well as the buffer solution. The use of the sulfohydryl compound in the buffer solution is hereinafter described in more detail. However, for the purposes of the coenzyme solution, a sulfohydryl compound may be added and generally the sulfohydryl compound in the buffer solution will have a sufficiently less oxidizing effect than the sulfohydryl compound used in the buffer solution. By adding the sulfohydryl compound to the coenzyme solution, it is possible to achieve a higher COK activity with less sulfohydryl compound in the total composition.

Thus, in this embodiment of the invention, the sulfohydryl compound N-acetyl cysteine is added next to the mixture in an amount sufficient to constitute a concentration in the range of 100 millimolar to 1 molar, preferably about 400 millimolar to about 800 millimolar. In the most preferred aspect, the N-acetyl cysteine or other sulfohydryl compound is added in an amount of about 600 millimolar.

After the addition of the two coenzymes, the pH is then adjusted, preferably with a tris buffer, namely [tris(hydroxymethyl)aminomethane] or any other buffer hereinafter described. In this respect, the NAD, the AMP and the N-acetyl cysteine are acidic in nature and any adjustment requires adjustment to raise the pH. In case the pH adjustment is excessive, adjustment can be achieved with acetic acid or other similar organic or inorganic acid. In this respect, it is always important to adjust the pH of both the substrate solution and the coenzyme solution prior to the addition of any enzyme inasmuch as the acid will have a deteriorating effect upon the enzyme. The enzymes may be added to the solutions in their dry lypholized state.

In place of the inhibiting coenzyme AMP, it is also possible to use sodium fluoride or other fluoride salts. Other acids, such as sulfuric acid and hydrochloric acid could also be used so long as it is not used in excessive amounts and so long as they do not inhibit any of the reaction mechanisms as hereinafter described. For example, a chloride salt or acid is a known inhibitor of the CPK reaction. Succinic acid is also an effective acid since it is non-inhibiting to any of the reactions hereinafter described.

After the pH of the coenzyme solution has been adjusted, the hexokinase enzyme may then be added. The hexokinase may range from about 10,000 I.U. per liter to about 500,000 I.U. per liter although the preferred range is about 50,000 I.U. to about 300,000 I.U. per liter. In the most preferred aspect, the hexokinase is added in an amount of about 200,000 I.U. per liter. Generally, the maximum amount of the enzyme HK, or for that matter the maximum amount of the enzyme G-6-PDH, is essentially unlimited except by virtue of cost factors and impurities contained therein. Normally, in most commercial applications, the amount of the enzyme present does not generally exceed about 10,000 I.U. per liter, in the final reaction mixture, i.e., after combining the three reagents to form the analytical assay medium.

The coenzyme solution is generally maintained at a pH within the range of about 5.0 to about 8.0. As indicated above, it is preferable to maintain an acid pH although the coenzyme NAD, and for that matter the coenzyme AMP, does not materially degrade at a pH of about 8.0. Nevertheless, since the HK/NAD combination is more stable at an acid pH, the preferred range is about 5.5 to about 7.0. In the most preferred aspect, the pH is established at about 6.0.

While the full mechanism for accomplishing the stabilization of the enzymes and coenzymes is not fully understood, it is believed that the selected solvent stabilizes the enzyme in the liquid media by protecting the functional group site, that is, the part of the molecule where a substrate reaction may actually occur, or is otherwise catalyzed. Moreover, stabilization is believed to occur by protecting the enzymes and coenzymes from microbial contamination and thus degradation. Selection of the proper pH for each of the solutions is also a significant factor in stabilizing the labile components. The coenzyme NAD differs from the coenzyme NADH in that the NAD will not appreciably dissolve in the selected solvent, such as propylene glycol. However, the NAD is more stable in water and the coenzymes do appear to be stabilized by the polyol. A pure polyol will denature the enzymes, but in the presence of an aqueous solution, such as a water-solvent mixture, the enzymes do not denature. Apparently, a polar group is required in the organic solvent to maintain the active sites of the enzymes in a stable condition. Obviously, some form of physical or chemical reaction occurs in the concentrated aqueous-organic solvent media, inasmuch as the enzymes and coenzymes retain catalytic activity and do not appreciably degrade in the specified concentrations.

BUFFER REAGENT

The buffer solution or buffer reagent will generally contain a buffering agent such as imidazole, often known as glyoxalin ($C_3H_4N_2$), or other buffering agent, as hereinafter described. In addition, the buffer solution will contain a metal activator such as a magnesium compound along with a sulfohydryl compound, as for example, dithiothreitol or dithioerithreitol. A carbohydrate polymer activator, such as dextran, may optionally be employed if desired. Furthermore, a sugar, such as glucose, is employed and which is a reactant in the coupling reactions.

In order to form the buffer solution, a suitable buffering agent, such as imidazole, as mentioned above, would be introduced into an aqueous vehicle. When imidazole is dissolved into water, it generally has a pH of about 9, but with a more efficient buffering capacity between a pH of about 5.0 to about 7.5. Thus, the pH is adjusted with acetic acid or other organic or inorganic acid. The pH of the buffer solution should be maintained within a pH range of about 4.0 to about 7.0 and preferably of about 5.0 to about 6.5. In the most preferred aspect, the pH is maintained at about 5.75.

The buffering agent, as for example, imidazole and similar azo compounds which may be employed, generally are added in an amount of about 0.01 molar to about 0.5 molar, although the preferred range is about 0.01 molar to about 0.15 molar. The most preferred amount of buffering agent is about 0.025 molar.

Other buffers which may be employed are Pipes Buffer, i.e., Piperazine - $N,N^1$ - bis (ethanesulfonic acid), Michaelis buffer, known also as the "Universal buffer" containing sodium acetate, diethyl barbituate, hydrochloric acid, and sodium chlorid, amino buffering agents, e.g. diethylamine or triethylamine, etc. may by employed. In addition, a combination of 0.1 to 1% of an alkali metal hydroxide and 0.5 to 3% of an alkali metal acid carbonate or phosphate may be used as a buffer. Generally, any buffering agent which does not interfere with stabilization and enzymatic reactivity and maintains a pH in the range of 4.0 to 7.0 may be used. In many cases, it may be desirable to employ a metal, such as magnesium, which activates the enzyme hexokinase in the coupling reaction when the stabilized composition is used. Magnesium, in the salt form of magnesium acetate, is one of the preferred agents for this purpose. However, magnesium aspartate, magnesium chloride, magnesium fluoride, etc. may be used. This agent does not have to be incorporated in the stabilized compositions of the present invention and may be added at the time of use. This agent, which activates the coupling enzymes should be used in an amount of about 5 millimolar to about 50 millimolar and, preferably, about 10 millimolar to about 35 millimolar. The most preferred amount is about 20 millimolar.

Thereafter, a sugar, glucose, is then added to the buffer solution. The glucose is presently added in a concentration of about 5 millimolar to about 500 millimolar, and in the preferred aspect, from about 10 millimolar to about 150 millimolar. The most preferred amount is 83 millimolar corresponding to about 1.5% w/v. Thus, in terms of weight concentration, the glucose is present in about 0.1 grams to about 5 grams per deciliter and in the preferred range, of about 0.5 grams to about 3 grams per deciliter. Other sugars in place of glucose could also be employed if desired.

The buffer solution also contains a polymer such as the carbohydrate polymer dextran as mentioned above. Dextran is not necessary, although desirable in some cases, and appears to serve as an activator in the final reaction. The dextran is usually added in a range of about 0.1 to about 5.0 gram percent and preferably from about 0.5 to about 3.0 gram percent. In the preferred aspect, the dextran is added in an amount of about 1.5 gram percent. The dextran generally ranges in molecular weight from about 10,000 to about 1,000,000 and the preferred fraction of dextran is that which has a molecular weight of about 200,000 to about 300,000. The exact mechanism by which the dextran creates an activation in the final reaction mechanism is not known, although it has been established that it does serve as an activator.

The polymer is preferably present in the stabilized solution up to an amount that remains in homogeneous suspension under refrigeration without precipitation. Any water-soluble polymers which are useful as activators or stabilizing agents in this invention are those which do not inhibit enzymatic activity. The polymer may act as a stabilizer in the final reaction mixture by entrapping the enzyme in the polymer matrix. The polymer may be a synthetic or organic origin. The dissolving of the polymer may be accelerated in the water by heating, generally to about 30° C. The rate at which the polymer is dissolved will increase with an increase in temperature.

The buffer solution also includes a sulfohydryl compound, such as dithiothreitol or dithioerithreitol, as mentioned above. Other sulfohydryl compounds, often known as R-SH compounds, which may be used, include many of the mercaptans such as mercaptoethanol, N-acetyl cysteine, which is used in the coenzyme or a combination of these, etc. Generally, any compound having a sulfohydryl group may be used, although it is desirable to prevent the use of any sulfohydryl compound which has an obnoxious odor. The sulfohydryl compound is generally added in a concentration of about 10 millimolar to about 200 millimolar with a preferred range of about 20 millimolar to about 180 millimolar. In the most preferred aspect, the sulfohydryl compound is added in an amount of about 65 millimolar.

As indicated previously, some sulfohydryl compounds could also be added to the coenzyme solution instead of the buffer solution so long as they do not denature the enzyme hexokinase. Dithiothreitol, for example, denatures hexokinase, whereas N-acetyl cysteine does not. When added to the coenzyme solution, the sulfohydryl compound will vary in a range of about 100 millimolar to about 1 molar, and preferably from about 250 millimolar to about 800 millimolar. In the most preferred aspect, in the coenzyme solution, the sulfohydryl compound is present in an amount of about 600 millimolar.

While the sulfohydryl compound acts as an activator, in high concentration it has a tendency to denature enzymes and other proteins. A polyol is capable of stabilizing the sulfohydryl compounds although strong sulfohydryl compounds cannot be included in the substrate or coenzyme solutions. However, sulfohydryl compounds, such as the N-acetyl crysteine can be included. The strong sulfohydryl compound also acts as a bactericidal agent which prevents microbial growth in the various solutions and to which it may be incorporated. Sulfohydryl compounds tend to decompose at alkaline pH; thus, for stability, the stabilizing medium is preferably kept at acid pH.

WORKING DETERMINATION COMPOSITION AND REACTIONS

In order to form a working solution, that is the solution to enable determination of the CPK constituent, the coenzyme reagent and substrate reagent solutions are first mixed together which results in a slightly alkaline pH of about 7 to 8. Generally, one part of coenzyme solution is added to about three parts of substrate solution. Thereafter, about 0.15 parts of the combined substrate coenzyme solution is added to about 1 part of the buffer solution. However, the combined reagents could be added to the buffer reagent in a range of 0.10 to about 0.34 parts to one part of the buffer reagent.

When the coenzyme solution is added to the substrate solution, substantial mixing should occur by repeated inversion. The premixed substrate-coenzymes solution is stable at room temperature for about ten days and is stable for about three months under refrigerated conditions. When the buffer reagent is added to the combined coenzyme-substrate reagent, gentle mixing should occur with repeated inversion. In this case, the combined composition is stable for about twelve hours at room temperature or for about seven days under refrigeration temperatures.

One of the unique advantages of the compositions of the present invention is that the various labile ingredients including the enzymes, coenzymes and substrates and other labile components are fully stabilized. Even more so, the final reaction product NADH is stabilized as produced by the CPK enzyme during the assay. In the absence of the compositions of the present invention, NADH degrades somewhat due to the acidic media required for the assay optimum pH of 5 to 7 for CPK.

When considering the reaction schemes set forth above for the analysis of CPK, it can be observed that the NADH or NADPH which is formed is measured photometrically and this is effectively a measure of the concentration of the CPK.

The reaction mechanisms for generating the NADH or the NADPH which is to be measured have been described above. However, myokinase enzyme is also present as an impurity in the G-6-PDH and the hexokinase enzymes as well as in the serum sample, or assay sample. The myokinase has a tendency to convert the ADP to AMP and ATP in a reversible reaction as follows:

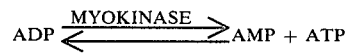

This latter reaction is undesirable since it is measured as false CPK activity. One of the phosphate moieties of the ATP coenzyme is attached to the glucose, thereby reducing the ATP to ADP. However, the ADP is a reactant in Reaction (1) in REACTION SCHEME 4 to create the creatine and ATP. This latter reaction in which ADP converts to AMP and ATP is undesirable inasmuch as the ATP will appear in Reaction (1) of REACTION SCHEME 4, thereby falsely elevating CPK values.

The AMP in the coenzyme solution is used to inhibit the formation of ATP by the law of mass action. The presence of the AMP will obviate excess formation of the ATP and will thereby stabilize the amount of the ATP present in the reaction media. Although AMP also inhibits the CPK reaction to a small extent, this inhibition is accepted in favor of eliminating the interference from myokinase.

The CPK enzyme, when introduced into the reaction medium, is activated by the sulfohydryl compounds. These sulfohydryl compounds are extremely unstable strong reducing agents. The hexokinase enzyme is effectively activated by the salts such as the magnesium salts although the CPK is essentially only activated by the sulfohydryl groups.

The creatine phosphate (CP) is fairly stable in the reaction medium except that the phosphate group of the CP tends to hydrolize in the presence of water, especially at acid pH. The hydrolization of the creatine phosphate would also tend to inhibit the reaction, i.e., product inhibition. It is desirable to provide a low amount of creatine in the reaction medium in order to prevent inhibition of Reaction (1) in REACTION SCHEME 4. The alkaline pH also tends to reduce the hydrolysis. Moreover, the glycerol or other organic solvent reduces the effect of hydrolysis. Thus, the organic solvent, along with the pH control, permits stabilization of the reagents and does not affect enzymatic reaction and determination in the preferred embodiment as described.

EXAMPLES

The invention is further illustrated by, but not limited to, the following examples.

EXAMPLE 1

A substrate solution is formed by adding glycerol to water at about 25° C. so that the glycerol is present in 30% v/v. A tris buffer is added in an amount of about 0.14 molar. Thereafter, 0.1% v/v of sodium azide is added to the solution. Creatine phosphate is added to the substrate solution in an amount of about 260 millimolars. Approximately 20 millimolar of ADP and 23 millimolar AMP are then added to the solution, and the pH is adjusted to about 8.2 by either 1 molar tris buffer or acetic acid. Thereafter, about 30,000 I.U. per liter of G-6-PDH is then added to the aqueous solution in order to form the substrate solution.

A coenzyme solution is formed by adding glycerol to water at about 25° C. so that the glycerol is present in an amount of about 50% v/v. Thereafter, the labile coenzyme NAD is added in an amount to form a final concentration of 100 millimoles. The AMP coenzyme is also added in an amount of about 86 millimolar. N-acetyl crysteine is dissolved next to form a final concentration of 600 millimolar. The pH is adjusted by addition of the tris-hydroxymethyl aminomethane so that the pH is about 6.0. Thereafter, hexokinase enzyme is added in an amount of about 200,000 I.U. per liter.

A buffer solution is formed by adding glucose to water to form a final concentration of 1.5 gram percent (83 millimolar) at about 20° C. In addition, imidazole is added as a buffering agent in an amount of about 0.025 molar. The imidazole when added has a pH of about 9 and glacial acetic acid is added in order to adjust the pH to about 6.0. Magnesium acetate is then added in an amount of about 20 millimolar. Dextran is then added in an amount of about 1.5 gram percent. Finally, dithiothreitol is added in an amount of 65 millimolar to complete the buffer solution. The substrate and coenzyme solutions are then poured into individual containers which are dark or amber glass, whereas the buffer solution may be stored in clear glass or plastic bottles sealed and stored under refrigeration temperatures.

The solutions are stabilized when unmixed for over one year. The substrate-coenzyme solutions may be combined (3 parts substrate+1 part coenzyme) and are stable at room temperature for about ten days and are stable for about three months under refrigerated conditions. When the buffer reagent is added to the combined coenzyme-substrate reagent, e.g. to each milliliter of buffer reagent add 0.15 milliliter of the substrate-coenzyme reagent composition, with gentle mixing, the combined composition is stable for about twelve hours at room temperature or for about seven days under refrigeration temperatures.

EXAMPLE 2

In order to perform a determination, the substrate solution and the coenzyme solution are then mixed such that 0.2 milliliters of the coenzyme reagent is added to about 0.6 milliliters of the substrate reagent. Thereafter, 150 microliters of the premixed substrate-coenzyme solution is added to one milliliter of the buffer reagent and mixed gently with repeated inversion. Thereafter, the CPK is added to the combined composition for determination. The working solution is stable at least 12 hours at room temperature and at least 7 days under refrigeration at 2°–8° C.

EXAMPLE 3

Example 1 is repeated except that a Michaelis buffer is used to adjust the pH to about 8.2. 0.1% v/v of a phenol bacteriostatic agent is added to the solution. The amount of ADP added to the solution is approximately 12 millimolar and approximately 27,000 I.U. per liter of G-6-PDH is added to the solution. Creatine phosphate is added to form a final concentration of 25 millimolar. In place of the glycerol, approximately 24% v/v of butanediol is used as the stabilizing agent.

In the coenzyme reagent, approximately 38% v/v of butane diol is added to the aqueous base as the stabilizing agent, and the pH is adjusted to approximately 6.2 by the addition of Michaelis buffer. The liable coenzyme NADP is used in place of NAD and is added in an amount of about 65 millimolars. The AMP coenzyme is added in an amount of 110 millimolars and the hexokinase enzyme is added in an amount of 85,000 I.U. per liter.

In the buffer reagent, 0.12 molar of Michaelis buffer is used as a buffering agent with the pH adjusted to about 6.2. Magnesium aspartate is used in place of the magnesium acetate and is added in an amount of about 31 millimolar.

EXAMPLE 4

The three reagents of Example 3 are mixed in order to perform a determination with 1 milliliter of a coenzyme reagent added to about 2.5 milliliters of the substrate reagent. Thereafter, 0.200 milliliters of the premixed substrate reagent and coenzyme reagent are added to one milliliter of the buffering reagent and mixed with repeated inversion. Thereafter, sample containing CPK is added to the composition for CPK determination. The same storage stability as found in Example 3 is also achieved.

EXAMPLE 5

Example 1 is repeated except that a sodium veronal or sodium barbitol buffer is added to the substrate reagent to adjust the pH to about 8.0. 0.1% pentachlorophenol bacteriostatic agent is added to the solution. The amount of ADP added to the solution is approximately 15 millimolar and the amount of creatine phosphate is 300 millimolar, and approximately 22,000 I.U. per liter of G-6-PDH is added to the solution. In place of the glycerol, approximately 37% v/v of 1,2-propanediol is used as the stabilizing agent.

In the coenzyme reagent, approximately 30% v/v of 1,2-propanediol is added to the aqueous base as the stabilizing agent, and the pH is adjusted to approximately 5.9 by the addition of a PIPES buffer. The liable coenzyme NAD is added in an amount of about 88 millimolars. The AMP coenzyme is added in an amount of 90 millimolars and the hexokinase enzyme is added in an amount of 125,000 I.U. per liter.

In the buffer reagent, 0.06 molar of PIPES buffer is used as a buffering agent with the pH adjusted to about 5.5. A surfactant, usually laurites, e.g. a sodium laurite is added (0.01% w/v) to prevent protein denaturation. Magnesium chloride is used in place of the magnesium acetate and is added in an amount of about 28 millimolar. Dithioerythritol is added at about 20 millimolar.

EXAMPLE 6

The three reagents of Example 5 are mixed in order to perform a determination with one milliliter of a coenzyme reagent added to about 3.0 milliliters of the substrate reagent. Thereafter, 0.120 milliliters of the premixed substrate reagent and coenzyme reagent are added to one milliliter of the buffering reagent and mixed with repeated inversion. Thereafter, sample containing CPK is added to the composition for CPK determination. The same storage stability as found in Example 5 is also achieved.

EXAMPLE 7

Example 1 is repeated except that 2-amino-2-methyl-1,3-propanediol buffer is added to the substrate reagent to adjust the pH to about 8.4. 0.22% v/v of a thymol bacteriostatic agent is added to the solution. The amount of ADP added to the solution is approximately 22 millimolar and approximately 44,000 I.U. per liter of G-6-PDH is added to the solution. In place of the glycerol, approximately 18% v/v of propylene glycol is used as the stabilizing agent.

In the coenzyme reagent, approximately 35% v/v propylene glycol is added to the aqueous base as the stabilizing agent, and the pH is adjusted to approximately 6.9 by the addition of a potassium biphthalate buffer. The labile coenzyme NADP is used in place of NAD and is added in an amount of about 92 millimolar. The AMP coenzyme is added in an amount of 150 millimolar and the hexokinase enzyme (from yeast) is added in an amount of 62,000 I.U. per liter.

In the buffer reagent, 0.10 molar of potassium biphthalate is used as a buffering agent with the pH adjusted to about 6.2. Magnesium fluoride is used in place of the magnesium acetate and is added in an amount of about 15 millimolar.

EXAMPLE 8

The three reagents of Example 7 are mixed in order to perform a determination with one milliliter of a coenzyme reagent added to about 2.5 milliliters of the substrate reagent. Thereafter, 0.18 milliliters of the premixed substrate reagent and coenzyme reagent are added to one milliliter of the buffering reagent and mixed with repeated inversion. Thereafter, a sample containing CPK is added to the composition for CPK determination. The same storage stability as found in Example 7 is also achieved.

It is to be realized that only preferred embodiments of the invention have been described and that numerous substitutions, modifications and alterations are permissible without departing from the spirit and scope of the invention as defined in the following claims.

Having thus described my invention, what I desire to claim and secure by Letters Patent is:

1. A multi-reagent liquid enzyme and coenzyme composition used in biological diagnostic determinations of biological constituents and which enzymes and coenzymes are normally unstable in an aqueous medium, said composition comprising:
    (a) a first liquid reagent comprised of:
        (1) at least 35% V/V of a non-reactive aqueous vehicle,
        (2) at least a sufficient amount of coenzyme to perform a determination dissolved in said aqueous vehicle and cooperating in a determination reaction, said coenzyme being normally unstable in the aqueous medium, and
        (3) an aqueous miscible polyol organic solvent dissolved in said aqueous vehicle in an amount of about 35% to about 55%, and which is liquid at least at room temperature when dissolved in said vehicle,
    (b) a second liquid reagent comprised of:
        (1) at least 35% V/V of a non-reactive aqueous vehicle,
        (2) an aqueous miscible polyol organic solvent dissolved in said aqueous vehicle in an amount of about 10% to about 50%, and which is liquid at least at room temperature when dissolved in said vehicle,
        (3) at least 5000 I.U. per liter of enzyme dissolved in said aqueous vehicle and cooperating in a determination reaction, said enzyme being normally unstable in the aqueous medium and normally reactive in the presence of the coenzyme in the aqueous medium, and
        (4) a labile substrate in said aqueous vehicle and cooperating in a determination reaction and which substrate is normally reactive with said enzyme in the aqueous medium in absence of being stabilized;
    (c) a third liquid reagent comprised of:
        (1) a non-reactive aqueous vehicle,
        (2) a buffering agent capable of maintaining a pH in said aqueous vehicle in a range sufficient to prevent degradation of a labile component, and
        (3) at least one additional labile component which is normally unstable in the aqueous media and capable of cooperating in and activating a determination reaction;
    (d) whereby said first and second and third reagents may be combined in proper amounts to form a working composition for a biological diagnostic determination so that the resultant composition in liquid form can be used for such determination, said composition being stabilized for a substantial period of time without significant degradation of the labile component and enzyme and coenzyme and substrate.

2. The composition of claim 1 further characterized in that said first reagent has a pH of from about 5.0 to about 8.0, such that the coenzyme is stabilized.

3. The composition of claim 2 further characterized in that said second reagent has a pH from about 7.0 to 10.0 such that the enzyme or substrate is stabilized.

4. The composition of claim 1 further characterized in that said first reagent includes at least 10,000 I.U. of enzyme dissolved in said aqueous vehicle and also cooperating in a determination reaction.

5. The composition of claim 4 further characterized in that said first reagent includes a sufficient amount of a second coenzyme to perform a determination dissolved in said aqueous vehicle and cooperating in a determination reaction.

6. The composition of claim 5 further characterized in that said second reagent also includes a coenzyme in an amount sufficient to perform a determination and dissolved in said aqueous vehicle and cooperating in a determination reaction.

7. The composition of claim 6 further characterized in that said enzymes are selected from the class consisting of glucose-6-phosphate dehydrogenase, hexokinase, glutamate dehydrogenase, pyruvate kinase and alkali phosphatase, and said coenzymes are selected from the class consisting of nicotinamide-adenine dinucleotide, adenosine triphosphate, adenosine-5'-diphosphate, nicotinamide-adenine dinucleotide phosphate, and adenosine monophosphate.

8. The composition of claim 6 further characterized in that
    (a) the coenzymes in said first reagent are adenosine monophosphate and nicotinamide-adenine dinucleotide or nicotinamide-adenine dinucleotide phosphate, the enzyme in said first reagent is hexokinase,
    (b) the coenzyme in said second reagent is adenosine-5'-diphosphate and the enzyme is glucose-6-phosphate dehydrogenase and the substrate is creatine phosphate, and
    (c) the additional labile component in said third reagent is a sulphydryl compound.

9. The composition of claim 8 further characterized in that the first reagent has a pH in the range of about 5 to about 8, said second reagent has a pH in the range of about 7 to about 10, and said third reagent has a pH in the range of about 4 to about 7.

10. The composition of claim 8 further characterized in that the first reagent has a pH in the range of about 5.5 to about 7.0, said second reagent has a pH in the range of about 8 to about 9, and said third reagent has a pH in the range of about 5 to about 6.5.

11. The composition of claim 1 further characterized in that said solvent has the following characteristics:
 (a) pH of 4 to 10;
 (b) liquid at room and refrigerator temperatures;
 (c) does not react with the coenzymes or enzymes other than forming electrostatic bonds;
 (d) miscible with water;
 (e) standard free energy of solvolysis is low.

12. The composition of claim 1 further characterized in that said third reagent comprises an R-SH compound as the additional labile component, and an organic polymer, and a sugar; and said second reagent comprises a bacteriostatic agent.

13. A method of stabilizing a labile enzyme and labile coenzyme and labile substrate in a multi-reagent composition used in biological diagnostic determinations of biological constituents, and which enzyme and coenzyme and substrate are normally unstable in an aqueous medium, said method comprising:
 (a) forming a first liquid stabilized reagent comprised of the steps of:
  (1) dissolving a coenzyme in at least 53% of V/V of an aqueous base in an amount sufficient to perform a determination and which coenzyme cooperates in a determination reaction, said coenzyme being normally unstable in the aqueous medium,
  (2) mixing said coenzyme containing aqueous base with about 35% to about 55% V/V of a nonreactive aqueous miscible polyol organic solvent to provide a stabilized composition and which solvent is dissolved in said base and liquid at least at room temperature when so dissolved, and
  (3) sealing the reagent in a first container;
 (b) forming a second liquid stabilized reagent comprising the steps of:
  (1) dissolving a labile substrate in at least 35% V/V of water and which substrate cooperates in a determination reaction,
  (2) mixing the water and dissolved substrate with about 10% to about 50% of an aqueous miscible polyol organic solvent to form a solution thereof and which organic solvent is dissolved in the water and liquid at least at room temperature when so dissolved,
  (3) dissolving at least 5000 I.U. per liter of enzyme in said solution to form the composition, and which enzyme cooperates in a determination reaction, said enzyme being normally unstable in the aqueous medium and normally reactive in the presence of said coenzyme, said enzyme also being normally reactive with said substrate in the aqueous medium and in absence of being stabilized,
  (4) sealing the reagent in a second container;
 (c) forming a third liquid stabilized reagent comprising the steps of:
  (1) mixing water with a buffering agent capable of maintaining an acid pH,
  (3) dissolving a labile component which is normally unstable in an aqueous media in the water and which component is capable of activating a determination reaction, and
  (3) sealing the third reagent in a third container;
 (d) whereby said first and second and third reagents may be dispensed from their respective containers and combined in proper amounts to form a working composition for a biological diagnostic determination so that the resultant composition in liquid form can be used for such determination, said composition being stabilized for a substantial period of time without significant degradation of the labile component and enzyme and coenzyme and substrate.

14. The method of stabilization of claim 13 further characterized in that said method comprises adding an agent to the aqueous base in said first reagent to maintain the reagent pH to about 5.0 to about 8.0.

15. The method of stabilization of claim 14 further characterized in that said method comprises adding an agent to said second reagent to maintain the reagent pH to about 7.0 to about 10.0.

16. The method of stabilization of claim 13 further characterized in that said method comprises dissolving at least 10,000 I.U. of enzyme in said aqueous vehicle of said first reagent and which enzyme also cooperates in a determination reaction.

17. The method of stabilization of claim 16 further characterized in that said method comprises dissolving a sufficient amount of a second coenzyme to perform a determination in said aqueous vehicle of said first reagent and which coenzyme also cooperates in a determination reaction.

18. The method of stabilization of claim 17 further characterized in that said method comprises dissolving a coenzyme in an amount sufficient to perform a determination in said water of said second reagent and which coenzyme also cooperates in a determination reaction.

19. The method of stabilization of claim 18 further characterized in that said enzymes are selected from the class consisting of glucose-6-phosphate dehydrogenase, hexokinase, glutamate dehydrogenase, pyruvate kinase and alkali phosphatase, and said coenzymes are selected from the class consisting of nicotinamideadenine dinucleotide, adenosine triphosphate, adenosine-5'-diphosphate nicotinamide-adenine dinucleotide phosphate, and adenosine monophosphate.

20. The method of stabilization of claim 18 further characterized in that:
 (a) the coenzymes in said first reagent are adenosine monophosphate and nicotinamide-adenine dinucleotide or nicotinamide-adenine dinucleotide phosphate, the enzyme in said first reagent is hexokinase,
 (b) the coenzyme in said second reagent is adenosine-5'-diphosphate and the enzyme is glucose-6-phosphate dehydrogenase and the substrate is creatine phosphate, and
 (c) the additional labile component in said third reagent is sulfhydryl compound.

21. The method of stabilization of claim 20 further characterized in that said method comprises adjusting the pH of the first reagent to a pH in the range of about 5 to about 8, adjusting the pH of said second reagent to a pH in the range of about 7 to about 10, and adjusting the pH of said third reagent to a pH in the range of about 4 to about 7.

22. The method of stabilization of claim 20 further characterized in that said method comprises adjusting the pH of the first reagent to a pH in the range of about 5.5 to about 7.0, adjusting the pH of said second reagent to a pH in the range of about 8 to about 9, and adjusting the pH of said third reagent to a pH in the range of about 5 to about 6.5.

23. The method of stabilization of claim 13 further characterized in that said method comprises using a solvent which has the following characteristics:
 (a) pH of 4 to 10;
 (b) liquid at room and refrigerator temperatures;
 (c) does not react with the coenzymes or enzymes other than forming electrostatic bonds;
 (d) miscible with water;
 (e) standard free energy of solvolysis is low.

24. The method of stabilization of claim 13 further characterized in that said method comprises dissolving an R-SH compound as the additional labile component, and an organic polymer and a sugar in said third reagent; and a bacteriostatic agent is dissolved in said first reagent.

25. The method of stabilization of claim 23 further characterized in that said method comprises mixing said water solution of said substrate with said organic solvent present in said second reagent in a range of about 20% to about 40% v/v.

26. The method of stabilization of claim 23 further characterized in that said method comprises mixing said aqueous base of said first reagent with said organic solvent present in said first reagent in about 50% v/v, and mixing said solution of water and substrate of said second reagent with said organic solvent present in said second reagent in about 30% v/v.

27. A stabilized coenzyme and enzyme containing reagent combinable with at least one other stabilized liquid reagent solution for use in the determination of creatine phosphokinase, said reagent comprising:
 (a) at least 35% v/v of an aqueous vehicle,
 (b) a polyol organic solvent in an amount of about 10% to about 50% v/v dissolved in said aqueous vehicle,
 (c) at least 5 millimolar of the labile coenzyme adenosine-5'-diphosphate,
 (d) at least 5000 I.U. per liter of the labile enzyme glucose-6-phosphate dehydrogenase,
 (e) at least 100 millimolar of the labile substrate creatine phosphate, and
 (f) said reagent being stabilized in a pH in the range of about 7 to about 10 and where said reagent can be mixed with a stabilized liquid reagent solution having an active coenzyme and active enzyme to form a working composition to enable a determination of creatine phosphokinase, and which reagent may be stored for a substantial period of time.

28. The stabilized reagent of claim 27 further characterized in that said reagent is stabilized in a pH in the range of about 8 to about 9.

29. The stabilized reagent of claim 27 further characterized in that the coenzyme adenosine-5'-diphosphate is present in an amount of about 5 millimoles to about 50 millimoles, the labile enzyme glucose-6-phosphate dehydrogenase is present in an amount of about 5000 I.U. per liter to about 100,000 I.U. per liter, and the substrate creatine phosphate is present in an amount of about 100 millimoles tto about 300 millimoles.

30. The stabilized reagent of claim 28 further characterized in that said organic solvent is present in an amount of about 20% v/v or about 40% v/v, the coenzyme adenosin-5'-diphosphate is present in an amount of about 10 millimoles to about 25 millimoles, the labile enzyme glucose-6-phosphate dehydrogenase is present in an amount of about 20,000 I.U. per liter to about 50,000 I.U. per liter, and the substrate creatine phosphate is present in an amount of about 200 millimoles to about 300 millimoles.

31. The reagent of claim 29 further characterized in that said organic solvent has the following characteristics:
 (a) pH between 4 to 10;
 (b) liquid at room and refrigerator temperatures;
 (c) does not react with enzymes other than forming electrostatic bonds;
 (d) miscible with water;
 (e) standard free energy of solvolysis is low.

32. The reagent of claim 31 further characterized in that the polyol contains from 2-10 carbon atoms and 2-4 hydroxyl groups.

33. The stabilized reagent of claim 29 further characterized in that said reagent comprises a bacteriostat which provides bacteriostatic action.

34. The stabilized reagent of claim 33 further characterized in that the bacteriostat is an azide compound.

35. A stabilized coenzyme and enzyme containing reagent combinable with at least one other stabilized liquid reagent solution for use in the determination of creatine phosphokinase, said reagent comprising:
 (a) at least 35% v/v of an aqueous vehicle,
 (b) a polyol organic solvent dissolved in said aqueous vehicle to be present in an amount of about 35% to about 55% v/v,
 (c) at least 20 millimolar of the labile coenzyme adenosine monophosphate,
 (d) at least 20 millimolar of the labile coenzyme nicotinamide-adenine dinucleotide or nicotinamide-adenine dinucleotide phosphate,
 (e) at least 10,000 I.U. per liter of the labile enzyme hexokinase, and
 (f) said reagent being stabilized in a pH in the range of about 5.0 to about 8.0 and where said reagent can be mixed with a stabilized liquid reagent solution having an active coenzyme and active enzyme to form a working composition to enable a determination of creatine phosphokinase, and which reagent may be stored for a substantial period of time.

36. The stabilized reagent of claim 35 further characterized in that said reagent is stabilized in a pH in the range of about 5.5 to about 7.0.

37. The stabilized reagent of claim 35 further characterized in that the coenzyme adenosin monophosphate is present in an amount of about 20 millimoles to about 150 millimoles, the coenzyme nicotinamide-adenine dinucleotide or nicotinamide adenine dinucleotide phosphate is present in an amount of about 20 millimoles to about 150 millimoles, the enzyme hexokinase is present in an amount of about 10,000 I.U. per liter to about 500,000 I.U. per liter.

38. The stabilized reagent of claim 36 further characterized in that the coenzyme adenosine monophosphate is present in an amount of about 35 millimoles to about 100 millimoles, the coenzyme nicotinamide-adenine dinucleotide or nicotinamide adenine dinucleotide phosphate is present in an amount of about 50 millimoles to about 100 millimoles, the enzyme hexokinase is present in an amount of about 50,000 I.U. per liter to about 250,000 I.U. per liter.

39. The stabilized reagent of claim 37 further characterized in that said organic solvent has the following characteristics:
 (a) pH between 4 to 10;

(b) liquid at room and refrigerator temperatures;
(c) does not react with coenzymes other than forming electrostatic bonds;
(d) miscible with water;
(e) standard free energy of solvolysis is low.

40. The reagent of claim 39 further characterized in that the polyol contains 2-4 hydroxyl groups and 2-10 carbon atoms.

41. A method of making a stabilized coenzyme and enzyme containing reagent combinable with at least one other stabilized liquid reagent solution for use in the determination of creatine phosphokinase, said method comprising:
   (a) dissolving a polyol organic solvent in an aqueous media so that the solvent is present in an amount of about 10% to about 50% v/v and the aqueous media is present in an amount of at least 35% v/v,
   (b) dissolving at least 5 millimolar of the labile coenzyme adenosine-5'-disphosphate in said media,
   (c) dissolving at least 5000 I.U. per liter of the labile enzyme glucose-6-phosphate dehydrogenase in said aqueous media,
   (d) dissolving at least 100 millimolar of the labile substrate creatine phosphate in said aqueous media, and
   (e) adjusting the pH of said reagent so that the components are stabilized in a pH in the range of about 7 to about 10, and where said reagent is adapted to be mixed with a stabilized liquid reagent solution having an active coenzyme and active enzyme to form a working composition to enable a determination of creatine phosphokinase, and which reagent may be stored for a substantial period of time.

42. The method of claim 41 further characterized in that said reagent is stabilized in a pH in the range of about 8 to about 9.

43. The method of claim 41 further characterized in that the coenzyme adenosine-5'-diphosphate is present in an amount of about 5 millimoles to about 50 millimoles, the labile enzyme glucose-6-phosphate dehydrogenase is present in an amount of about 5000 I.U. per liter to about 100,000 I.U. per liter, and the substrate creatine phosphate is present in an amount of about 100 millimoles to about 300 millimoles.

44. The method of claim 42 further characterized in that said organic solvent is present in an amount of about 20% v/v to about 40% v/v, the coenzyme adenosine-5'-diphosphate is present in an amount of about 10 millimoles to about 25 millimoles, the labile enzyme glucose-6-phosphate dehydrogenase is present in an amount of about 20,000 I.U. per liter to about 50,000 I.U. per liter, and the substrate creatine phosphate is present in an amount of about 200 millimoles to about 300 millimoles.

45. The method of claim 43 further characterized in that said solvent has the following characteristics:
   (a) pH of 4 to 10;
   (b) liquid at room and refrigerator temperatures;
   (c) does not react with the coenzymes or enzymes other than forming electrostatic bonds;
   (d) miscible with water;
   (e) standard free energy of solvolysis is low.

46. A method of making a stabilized coenzyme and enzyme containing reagent combinable with at least one other stabilized liquid reagent solution for use in the determination of creatine phosphokinase, said method comprising:
   (a) dissolving a polyol organic solvent in an aqueous media so that the solvent is present in an amount of about 35% v/v to about 55% v/v and the aqueous media is present in an amount of at least 35% v/v,
   (b) dissolving at least 20 millimolar of the labile coenzyme adenosine monophosphate in said media,
   (c) dissolving at least 20 millimolar of the labile coenzyme nicotinamide-adenine dinucleotide or nicotinamide-adenine dinucleotide phosphate in said aqueous media,
   (d) dissolving at least 10,000 I.U. per liter of the labile enzyme hexokinase in said aqueous media, and
   (e) adjusting the pH of said reagent so that the components are stabilized in a pH in the range of about 5.0 to about 8.0 and where said reagent is adapted to be mixed with a stabilized liquid form a working composition to enable a determination of creatine phosphokinase, and which reagent may be stored for a substantial period of time.

47. The method of claim 46 further characterized in that said reagent is stabilized in a pH in the range of about 5.5 to about 7.0.

48. The method of claim 46 further characterized in that the coenzyme adenosine monophosphate is present in an amount of about 20 millimoles to about 150 millimoles, the coenzyme nicotinamide-adenine dinucleotide or nicotinamide adenine dinucleotide phosphate is present in an amount of about 20 millimoles to about 150 millimoles, and the enzyme hexokinase is present in an amount of about 10,000 I.U. per liter to about 500,000 I.U. per liter.

49. The method of claim 47 further characterized in that the coenzyme adenosine monophosphate is present in an amount of about 35 millimoles to about 100 millimoles, the coenzyme nicotinamide-adenine dinucleotide or nicotinamide adenine dinucleotide phosphate is present in an amount of about 50 millimoles to about 100 millimoles, and the enzyme hexokinase is present in an amount of about 50,000 I.U. per liter to about 250,000 I.U. per liter.

50. The method of claim 48 further characterized in that said solvent has the following characteristics:
   (a) pH of 4 to 10;
   (b) liquid at room and refrigerator temperatures;
   (c) does not react with the coenzymes or enzymes other than forming electrostatic bonds;
   (d) miscible with water;
   (e) standard free energy of solvolysis is low.

51. The composition of claim 1 further characterized in that said first reagent includes a sufficient amount of a second coenzyme and a sulfohydryl compound to perform a determination dissolved in said aqueous vehicle and cooperating in a determination reaction.

52. The method of stabilization of claim 13 further characterized in that said method comprises dissolving a sufficient amount of a second coenzyme and a sulfohydryl compound to perform a determination in said first reagent and which coenzyme and sulfohydryl compound also cooperates in a determination reaction.

53. The method of stabilization of claim 52 further characterized in that said sulfohydryl compound is N-acetyl cysteine.

54. The method of stabilization of claim 13 further characterized in that said method comprises dissolving a sulfohydryl compound as the additional labile component in said third reagent, and an organic polymer and a sugar in said third reagent; and dissolving a bacteriostatic agent and a sulfohydryl compound in said first reagent.

55. The method of stabilization of claim 54 further characterized in that the sulfohydryl compound in the third reagent is selected from the class consisting of dithiothreitol, dithioerithreitol, N-acetyl cysteine and cysteine.

56. A multi-reagent liquid enzyme and coenzyme composition used in biological diagnostic determinations of creatine phosphokinase and which enzymes and coenzymes are normally unstable in an aqueous medium, said composition comprising:

(a) a first reagent comprised of:
  (1) at least 35% v/v of a non-reactive aqueous vehicle,
  (2) about 35% to about 55% of an aqueous miscible polyol organic solvent dissolved in said aqueous vehicle and which is liquid at least at room temperatures when dissolved in said vehicle,
  (3) at least 20 millimolar of the labile coenzyme adenosine monophosphate dissolved in said aqueous vehicle, said coenzyme being normally unstable in the aqueous medium,
  (4) at least 20 millimolar of the labile coenzyme nicotinamide-adenine dinucleotide or nicotinamide-adenine dinucleotide phosphate dissolved in said aqueous vehicle and cooperating in a determination reaction,
  (5) at least 10,000 I.U. per liter of the labile enzyme hexokinase, and
  (6) said reagent being stabilized in pH in the range of about 5.0 to about 8,0, said enzymes being normally unstable in the aqueous medium and normally reactive in the presence of the coenzymes in the aqueous medium;

(b) a second reagent comprised of:
  (1) at least 35% v/v of a non-reactive aqueous vehicle,
  (2) about 10% to about 50% of an aqueous miscible polyol organic solvent dissolved in said aqueous vehicle and which is liquid at least at room temperature when dissolved in said aqueous vehicle,
  (3) at least 5 millimolar of the labile coenzyme adenosine-5'-diphosphate, said coenzyme being unstable in the aqueous medium,
  (4) at least 5000 I.U. per liter of the libale enzyme glucose-6-phosphate dehydrogenase dissolved in said aqueous vehicle and cooperating in a determination reaction, said enzyme being unstable in the aqueous medium,
  (5) at least 100 millimolar of the labile substrate creatine phosphate in said aqueous vehicle and cooperating in a determination reaction, and
  (6) said reagent having a pH of about 7 to about 10;

(c) a third reagent comprised of:
  (1) a non-reactive aqueous vehicle;
  (2) a buffering agent capable of maintaining a pH in said aqueous vehicle in a range sufficient to prevent degradation of a labile component, and
  (3) at least one additional labile component which is normally unstable in an aqueous media and capable of cooperating in and activating a determination reaction;

(d) whereby said first and second and third reagents may be combined in proper amounts to form a working composition for a biological diagnostic determination so that the resultant composition in liquid form can be used for such determination and where each of said reagents are stabilized for a substantial period of time without significant degradation of the labile component and enzyme and coenzyme and substrate.

* * * * *